US009176115B2

(12) United States Patent
Tavana et al.

(10) Patent No.: US 9,176,115 B2
(45) Date of Patent: Nov. 3, 2015

(54) ENGINEERING INDIVIDUALLY ADDRESSABLE CELLULAR SPHEROIDS USING AQUEOUS TWO-PHASE SYSTEMS

(71) Applicants: Hossein Tavana, Hudson, OH (US); Ehsan Atefi, Akron, OH (US); Stephanie Lemmo Ham, Akron, OH (US)

(72) Inventors: Hossein Tavana, Hudson, OH (US); Ehsan Atefi, Akron, OH (US); Stephanie Lemmo Ham, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 14/064,886

(22) Filed: Oct. 28, 2013

(65) Prior Publication Data

US 2014/0120573 A1    May 1, 2014

Related U.S. Application Data

(60) Provisional application No. 61/718,775, filed on Oct. 26, 2012.

(51) Int. Cl.
*G01N 33/50* (2006.01)
*C12N 5/00* (2006.01)

(52) U.S. Cl.
CPC .......... *G01N 33/5011* (2013.01); *C12N 5/0062* (2013.01); *G01N 33/5008* (2013.01); *G01N 33/5073* (2013.01); *C12N 2500/50* (2013.01)

(58) Field of Classification Search
None
See application file for complete search history.

(56) References Cited

FOREIGN PATENT DOCUMENTS

WO    WO 2012131000 A1 * 10/2012

OTHER PUBLICATIONS

Absolom, DR; et al; "Endothelialization of polymer surfaces" Journal of Biomedical Material Research, 22, 271-285, 1988.*
Tavana, Hossein; et al; "Polymeric Aqueous Biphasic Systems for Non-Contact Cell Printing on Cells: Engineering Heterocellular Embryonic Stem Cell Niches" Advanced Materials, 22, 2628-2631, 2010.*
Morrow, K. John; "3-D Cell Culture Takes Research Deeper : In Vivo-Like Environment Paves Way toward Fresh Insights and Whole-Organ Generation" Genetic Engineering & Biotechnology News, 31, 30-33, 2011.*
Yu Fang, ME; et al; "Rapid Generation of Multiplexed Cell Cocultures Using Acoustic Droplet Ejection Followed by Aqueous Two-Phase Exclusion Patterning" Tissue Engineering: Part C, 18, 647-657, 2012.*
Tung, et al., High-throughput 3D spheroid culture and drug testing using a 384 hanging drop array, Analyst, 2011, 136, 473-478.
Tavava, et al., Rehydration of Polymeric, Aqueous, Biphasic System Facilitates High Throughput Cell Exclusion Patterning for Cell Migration Studies, Adv. Funct. Mater. 2011, 21, 2920-2926.

* cited by examiner

*Primary Examiner* — Blaine Lankford
*Assistant Examiner* — David Berke-Schlessel
(74) *Attorney, Agent, or Firm* — Renner Kenner Greive Bobak Taylor & Weber

(57) ABSTRACT

Provided is multi-phase systems that may be used to prepare a three-dimension aggregate of cells referred to as a cellular spheroid. The multi-phase system includes a droplet of an aqueous polymer phase within an immersion aqueous polymer phase. The droplet of the droplet aqueous polymer phase contains a three-dimensional aggregate of cells (cellular spheroid). Types of cells that may be used in the multi-phases system include stem cells and cancer cells. The cellular spheroids with the multi-phase system may be used to monitor cell growth in three-dimensional systems, or screen drugs in a three-dimension aggregate of cells.

12 Claims, 10 Drawing Sheets

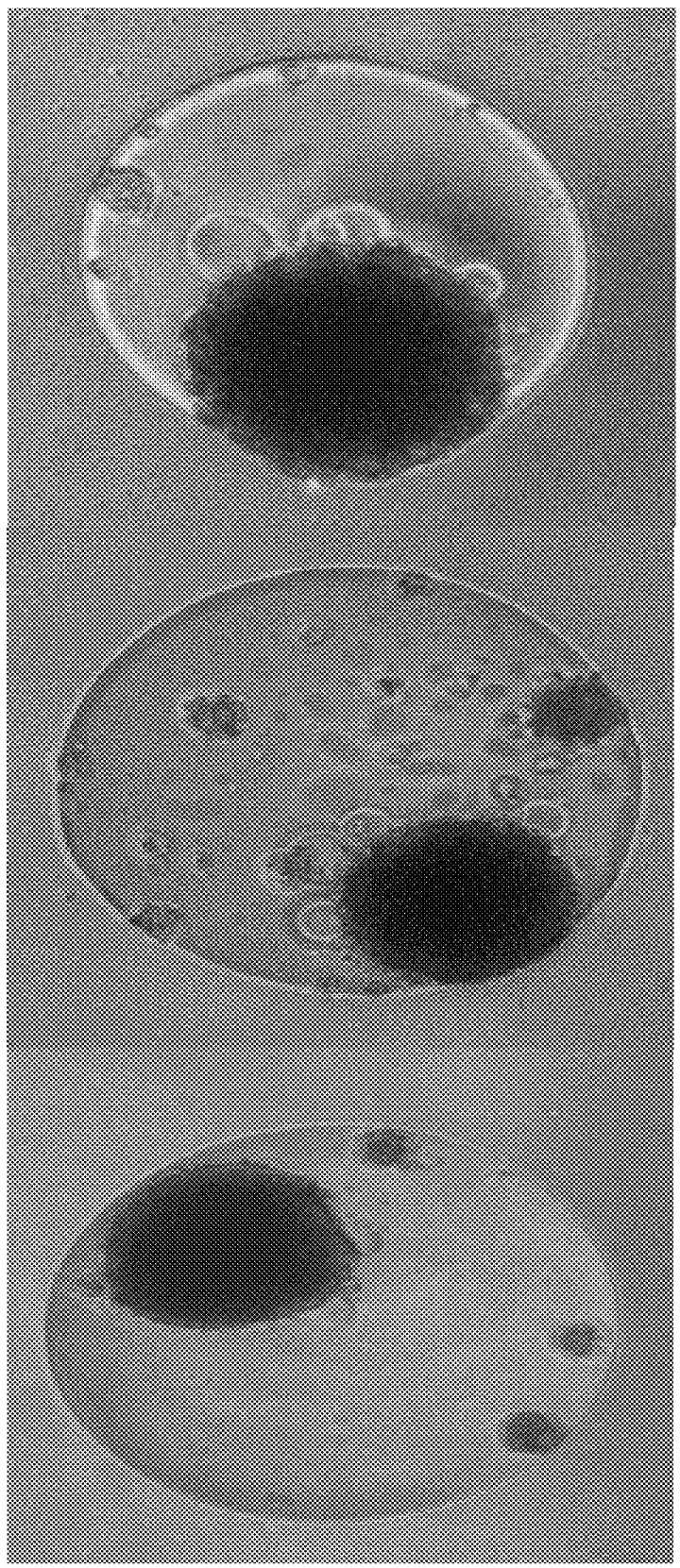

ENGINEERING INDIVIDUALLY
ADDRESSABLE CELLULAR SPHEROIDS
USING AQUEOUS TWO-PHASE SYSTEMS

CROSS-REFERENCE TO RELATED
APPLICATIONS

This application claims priority from U.S. Provisional Patent Application No. 61/718,775 filed on Oct. 26, 2012, the contents of which are incorporated herein by reference.

FIELD OF THE INVENTION

The present invention relates to three dimensional cell aggregates or "cellular spheroids." More particularly the present invention provides a cellular spheroid in an aqueous two-phase system, methods of preparing a cellular spheroid in an aqueous two-phase system, and methods of screening a drug with a cellular spheroid in an aqueous two-phase system.

BACKGROUND OF THE INVENTION

Conventional two-dimensional cultures of cancer cells are widely used for evaluating potential anti-cancer drugs. However, growing evidence shows that cancer cells respond differently to anticancer drugs in a two-dimensional monolayer culture than they would in vivo, where cells reside in a three-dimensional environment. To more accurately model the effects of potential drugs in vivo a three dimensional aggregate of cells, or cellular spheroid, is desired. Presently, the hanging drop method is used to produce cancer cell spheroids for anti-cancer drug screening. The hanging drop method, which produces spheroids by suspending cells in droplets of medium, suffers from several shortcomings. For instance, surface tension limits the maximum size of a drop prepared by the hanging drop method, also, due to the small size of the suspended drops, evaporation is a large concern. As the water within the drop evaporates, the concentration of soluble components such as proteins and salts in the medium increases, subjecting the cells to a changing osmotic pressure, thus compromising their normal morphology and function. The media also needs to be refreshed daily to avoid the build up of cell waste and because of the small volume of media available to the cells. The exchange of media is generally done by hand, using a pipette, increasing the likelihood of incorporating errors such as aspirating out spheroids from hanging drops or introducing shear stress to cells due to manual pipetting. In addition, treating spheroids with exact drug concentrations is a challenge due to the presence of existing media. The hanging drop method is also sensitive to physical movements that can result in the detachment of drops and the spheroids within from the surface from which the drops hang.

Presently, a need exists for methods of screening drug compounds in three-dimensional cultures that do not suffer from the above problems, and thus enable reliable, high throughput screening of potential drug compounds.

SUMMARY OF THE INVENTION

An embodiment of the present invention provides an aqueous two-phase system for cell aggregates comprising: an immersion aqueous polymer phase; and, within the immersion aqueous polymer phase, a droplet of a droplet aqueous polymer phase containing a three-dimensional aggregate of cells.

Another embodiment provides a method of producing a cellular spheroid comprising the steps of: providing a well containing a immersion aqueous polymer phase; inserting a droplet of a droplet aqueous polymer phase; inserting cells into the droplet aqueous polymer phase; and allowing the cells to self assemble into a spheroid.

Another embodiment provides a method of screening potential drugs comprising: providing an aqueous two-phase system for the production of cell spheroids comprising a immersion aqueous polymer phase, and within the immersion aqueous polymer phase, a droplet of a droplet aqueous polymer phase containing a cellular spheroid; administering a potential drug; and monitoring the cellular spheroid.

BRIEF DESCRIPTION OF THE DRAWINGS

FIG. 9A provides the resulting spheroids from a 5,000 cells/0.3 µl density using MDA-MB-157 cells.

FIG. 9B provides the resulting spheroids from a 10,000 cells/0.3 µl densitys using MDA-MB-157 cells.

FIG. 9C provides the resulting spheroids from a 5,000 cells/0.3 µl density using MDA-MB-157 cells.

Figure 1A:
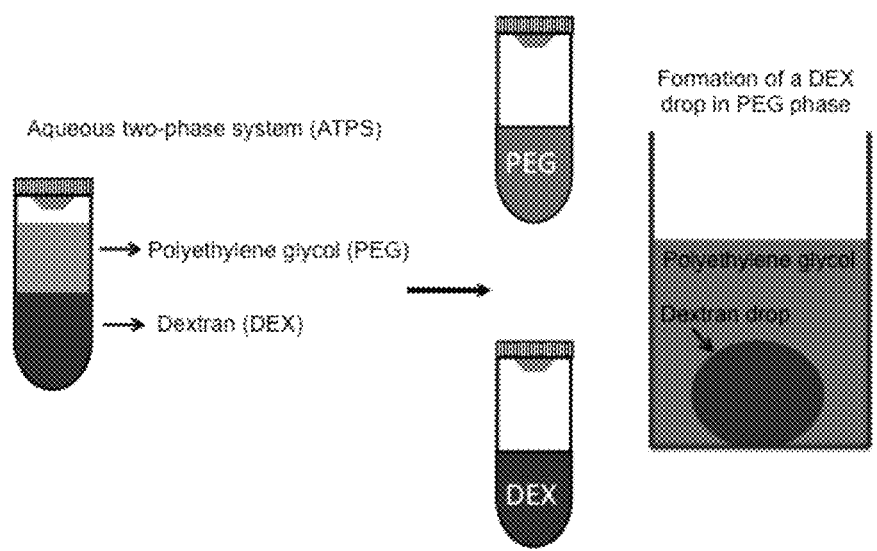
FIG. 1A provides a schematic of one or more embodiments of an aqueous two-phase system made from culture media and polyethylene glycol and dextran as two phase-forming polymers. Dextran phase is denser and can form a drop within the PEG phase sitting on the surface, if a small volume of the DEX phase is dispensed into the PEG phase.

DETAILED DESCRIPTION OF ILLUSTRATIVE
EMBODIMENTS

In one or more embodiments, an aqueous multi-phase system is provided comprising a first aqueous polymer phase which may be referred to as an immersion aqueous polymer phase or immersion phase, and within the immersion aqueous polymer phase, a droplet of a second aqueous polymer phase, which may be referred to as a droplet aqueous polymer phase or droplet phase. Cells may be placed in the droplet of the droplet aqueous polymer phase to produce a three-dimensional aggregate of cells, or cellular spheroid.

The aqueous multi-phase system includes at least two aqueous polymer phases that are immiscible with each other. The immiscible aqueous polymer phases, if mixed, form distinct phases that can separate. The aqueous polymer phases may be immiscible because a polymer in an aqueous polymer phase has property that repels the polymer in another aqueous polymer phase. For instance, an imersion aqueous polymer phase may by hydrophobic and repel the polymers in a hydrophilic droplet aqueous polymer to form separate phases.

In one or more embodiments, the immersion aqueous polymer phase is less dense than the second aqueous polymer phase. In these embodiments, a droplet polymer phase will reside at the bottom of the immersion aqueous polymer phase. In other embodiments, the immersion aqueous polymer phase is more dense than the droplet aqueous polymer phase. In these embodiments, the droplet polymer phase will reside at the top of the immersion aqueous polymer phase. In these or other embodiments, the multi-phase system may be a three-phase system, where the droplet aqueous polymer phase is less dense than the immersion aqueous polymer phase, but more dense than a third aqueous polymer phase. In these embodiments, the droplet polymer phase will reside at the interface of where the immersion and third aqueous polymer phase meet.

In one or more embodiments, the total volume of the multi-phase polymer system is large enough to avoid the deleterious effects of solvent evaporation. The solvent evaporation, and its effects, may be limited by using larger total volumes of the multi-phase polymer system. This allows the multi-phase polymer system to be used for long term cell cultures. Herein, a long term cell culture is one in which cells can be cultured for greater than one week. Further, because the multi-phase polymer system does not require the use of a hanging drop, the total volume is not limited to the volume that can be suspended. Thus, the maximum volume of multi-phase polymer system is limited by pragmatic concerns. In these or other embodiments, a long term culture may be 6 to 8 weeks. In one or more embodiments, the multi-phase polymer system has a total volume of greater than 10 µL, in other embodiments, greater than 25 µL, and in still other embodiments, greater than 50 µL.

The use of the term "droplet" herein refers to the size and shape of the droplet phase, and does not necessarily reflect how the droplet phase is formed or introduced into the first phase. In one or more embodiments, the droplet of the droplet aqueous polymer phase is essentially spherical. A droplet that is essentially spherical refers to a droplet shape that is spherical or close to spherical and has a round surface without any flat spots or with only minimal flat spots.

The droplet may be characterized by the volume of the droplet. In one or more embodiments the droplet has a volume of less than 1000 nL, in other embodiments, less than 500 nL, and in still other embodiments, less than 300 nL. In these or other embodiments, the droplet has a volume of greater than 20 nL, in other embodiments, greater than 50 nL, and in still other embodiments, greater than 100 nL. In certain embodiments the droplet has a volume of about 20 nL to about 1000 nL, in other embodiments, of about 50 nL to about 500 nL, and in still other embodiments, of 100 nL to about 300 nL.

The droplet may also be characterized by its volume percentage of the total aqueous multi-phase system. In one or more embodiments, the droplet makes up less than 0.02%, in other embodiments, less than 0.01% and in still other embodiments, less than 0.005% of the total aqueous multi-phase system. In these or other embodiments, the droplet has a percent volume of greater than 0.0001%, in other embodiments, greater than 0.0002%, and in still other embodiments, greater than 0.0004% the total aqueous multi-phase system. In certain embodiments, the droplet has a percent volume of about 0.02% to about 0.0001%, in other embodiments, of about 0.01% to about 0.0002%, and in still other embodiments, of about 0.005% to about 0.0004% the total aqueous multi-phase system.

Each aqueous polymer phase comprises a polymer dissolved in water. The amount of polymer dissolved in water may be described by the percent weight of polymer in total weight of the aqueous polymer phase. It should be noted that, with smaller polymers are used, typically a larger percent weight of polymer is needed to properly form separate aqueous polymer phases with another aqueous polymer. In one or more embodiments, the amount of polymer is less than 20%, in other embodiments, less than 18%, and in still other embodiments, less than 15% by weight of the aqueous polymer phase. In these or other embodiments, the amount of polymer is greater than 5%, in other embodiments, greater than 6%, and in still other embodiments, greater than 8% by weight of the aqueous polymer phase. In certain embodiments, the amount of polymer is about 5% by weight to about 20% by weight in other embodiments, of about 6% by weight to about 18% by weight, and in still other embodiments, of about 8% by weight to about 15% by weight of the aqueous polymer phase.

The polymer of the first aqueous polymer phase and the polymer of the second aqueous polymer phase in a two-phase polymer system may be referred to as a polymer pair. While other polymer pairs may be used to prepare a two-phase polymer system, for ease of illustration, the polymer pair of polyethylene glycol "PEG" and dextran "DEX" will be discussed in further detail to describe the aqueous polymer phases.

Figure 1B:
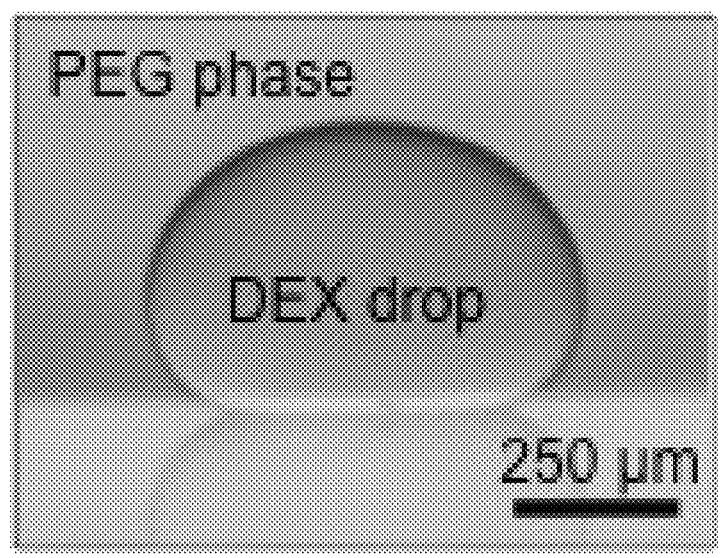
FIG. 1B provides an actual image of one or more embodiments of a multi-phase system where a DEX drop is formed within the immersion PEG phase.

A two-phase polymer system may be prepared with either an aqueous polymer phase of dextran, which may be referred to as a dextran phase, or polyethylene glycol, which may be referred to as a polyethylene glycol phase as the immersion aqueous polymer phase. Because the dextran phase is denser than the polyethylene glycol phase, the dextran phase will reside at the bottom of the two-phase as seen in FIG. 1. A third, aqueous polymer phase may be added to produce a three-phase system. If the third phase is denser than both the polyethylene glycol phase and the dextran phase the dextran phase will reside as a droplet between the two phases.

A two-phase system may also be prepared from a dextran phase and a polyethylene glycol phase, where dextran is the immersion aqueous polymer phase. In this two-phase system, polyethylene glycol phase is the droplet aqueous polymer phase, and will reside at the top of the two-phase system. Again, a third, aqueous polymer phase may be added to produce a three-phase system. If the third phase is less dense than both the polyethylene glycol phase and the dextran phase the polyethylene glycol phase will reside as a droplet between the two phases.

Suitable dextran polymers for use as a dextran phase may be characterized by their molecular weight. In one or more embodiments, the molecular weight of the dextran polymer is less than 2,000,000 g/mol, in other embodiments, less than 1,000,000 g/mol, and in still other embodiments, less than 500,000 g/mol the total aqueous multi-phase system. In these or other embodiments, the molecular weight of the dextran polymer is greater than 1000 g/mol, in other embodiments, greater than 10,000 g/mol, and in still other embodiments, greater than 40,000 g/mol the total aqueous multi-phase system. In certain embodiments, the molecular weight of the dextran polymer is about 1000 g/mol to about 2,000,000 g/mol, in other embodiments, of about 10,000 g/mol to about 1,000,000 g/mol, and in still other embodiments, of about 40,000 g/mol to about 500,000 g/mol the total aqueous multi-phase system.

Suitable polyethylene glycol polymers for use as a polyethylene glycol phase may be characterized by their molecular weight. In one or more embodiments, the molecular weight of the polyethylene glycol polymer is less than 35,000 g/mol, in other embodiments, less than 20,000 g/mol, and in still other embodiments, less than 13,000 g/mol the total aqueous multi-phase system. In these or other embodiments, the molecular weight of the polyethylene glycol polymer is greater than 100 g/mol, in other embodiments, greater than 1,000 g/mol, and in still other embodiments, greater than 4,000 g/mol the total aqueous multi-phase system. In certain embodiments, the molecular weight of the polyethylene glycol polymer is about 100 g/mol to about 35,000 g/mol, in other embodiments, of about 1,000 g/mol to about 20,000 g/mol, and in still other embodiments, of about 4,000 g/mol to about 13,000 g/mol the total aqueous multi-phase system.

Again, other polymer pairs may be used to prepare a two-phase polymer system as long as the polymers meet the minimum concentration at a specific molecular weight to separate into different phases. Examples of polymer pairs other than polyethylene glycol and dextran suitable for preparing a two phase polymer system include, but are not limited to, any two polymers selected from the group consisting of polyethylene glycol, polyacrylamide, ficoll, poly(methyl methacrylate), and hydroxypropyl.

Any type of cells that exist in a three-dimensional environment in vivo may be used in the multi-phase system to produce a cellular spheriod. In one or more embodiments, more than one type of cell may be used in the multi-phase system to provide a multicellular three-dimensional aggregate that contains at least two different types of cells.

In one or more embodiments, the cells in the multi-phase system may be stem cells. An example of a type of stem cell includes, but is not limited to, embryonic stem cells. The multi-phase system with embryonic stem cells may be used for the study of normal embryonic development.

In one or more embodiments, the cells in the multi-phase system may be cancer cells. The multi-phase system with cancer cells may be used to model tumor growth. The multi-phase system also provides an ideal environment for in vitro testing of potential drugs to inhibit tumor growth or eliminate cancer. Examples of cancer cells include but are not limited to breast cancer, prostate cancer, liver cancer, lung cancer, ovarian cancer, and sarcomas cancer.

In one or more embodiments, cancer cells may be obtained from a cancer patient. In these or other embodiments, cancer cells from a cancer patient are retrieved during surgery and maintained as tumor xenograft in mouse. The cells may then be placed in a multi-phase polymer system to produce cellular spheroids.

In one or more embodiments, the multiphase system includes cell media. Any aqueous polymer phase within the multi-phase system may include cell media. Cell media may be included in the first polymer phase, the second polymer phase, any additional polymer phases, or any combination thereof. Those skilled in the art will appreciate the particular cell media required for the type of cells and the cellular spheroids desired. Examples of cell media include, but are not limited to, Dulbecco's modified eagle medium and alpha minimum essential medium supplemented with serum and other necessary ingredients.

In one or more embodiments, the multiphase system includes an extracellular matrix. Any aqueous polymer phase within the multi-phase system may include an extracellular matrix material. An extracellular matrix may be included in the first polymer phase, the second polymer phase, any additional polymer phases, or any combination thereof. The extracellular matrix may be used to provide structural support for cells, regulating intercellular communication, or regulating communication between the cells and the extracellular matrix itself. Examples of extracellular matrix material include, but are not limited to, collagen, laminin, fibronectin, matrigel, elastin, and combinations thereof.

In one or more embodiments, the multi-phase system can be contained in what will be referred to as a well. Broadly, a well simply provides a holding volume for holding the multi-phase system. The well may be depression formed with suitable structure and a bottom surface that is round, flat, or conical. In other embodiments, the multi-phase system can be may be supported on a flat bottom surface and the surface tension of the phases will allow the immersion phase of the multi-phase system to form a bead or hemispherical shape. Regardless, the multi-phase system is supported by or contained in depression that includes a bottom surface. In one or more embodiments, the droplet has minimal contacts with the bottom surface. Minimal contacts with the bottom surface refers to the droplet's ability to form a substantially spherical shape providing a limited contact area between the bottom surface and the droplet. Ideally, a droplet should have a contact angle as close as possible to 180°.

In one or more embodiments, the bottom surface is non-adherent to cells. Typically, a surface that is non-adherent to cells has been treated with a coating that greatly reduces the binding of attachment proteins produced by the cells, thus minimizing cell attachment. Examples of commercially available plates, dishes, or flasks with a bottom surfaces that are non-adherent to cells include ultra-low attachment plates available from Corning.

In one or more embodiments, a plurality of multi-phase systems may be prepared on the same apparatus, which may be referred to as a plate. In these or other embodiments, when the multiphase system is contained in a well, a plate may have a number of wells. Examples of plates with a number of wells includes, but is not limited to, 6 well plates, 24 well plates, 96 well plates, and 384 well plates. In other embodiments, where the multi-phase system is on a flat bottom surface, the flat bottom surface may be a plate with any number of multi-phase systems.

An aqueous multi-phase system may be used to produce cellular spheroids from cells. In one or more embodiments, a cellular spheroid may be prepared by providing a first aqueous polymer phase; inserting a droplet of a second aqueous polymer phase; inserting cells into the second aqueous polymer phase; and allowing the cells to self assemble into a spheroid.

In one or more embodiments, the droplet of the second aqueous polymer phase may be inserted into the first aqueous polymer phase by pipetting second aqueous polymer phase into the first aqueous polymer phase. In one or more embodiments, the second phase and cells are premixed prior to being inserted into the first aqueous polymer phase. In these embodiments, cells and the second aqueous polymer phase are inserted into the first polymer phase together.

In one or more embodiments, a cell culture media may be included by premixing an aqueous polymer phase with the extracellular matrix. In these or other embodiments, it may be advantageous to refresh the cell culture media. Refreshing of cell culture media is typically performed by removing a portion of the cell culture media within the two phase system and replacing it with new cell culture media. Additional culture media may be added to replace any volume of liquid lost to evaporation.

In one or more embodiments, an extracellular matrix may be included by premixing an aqueous polymer phase with the extracellular matrix.

Figure 2:
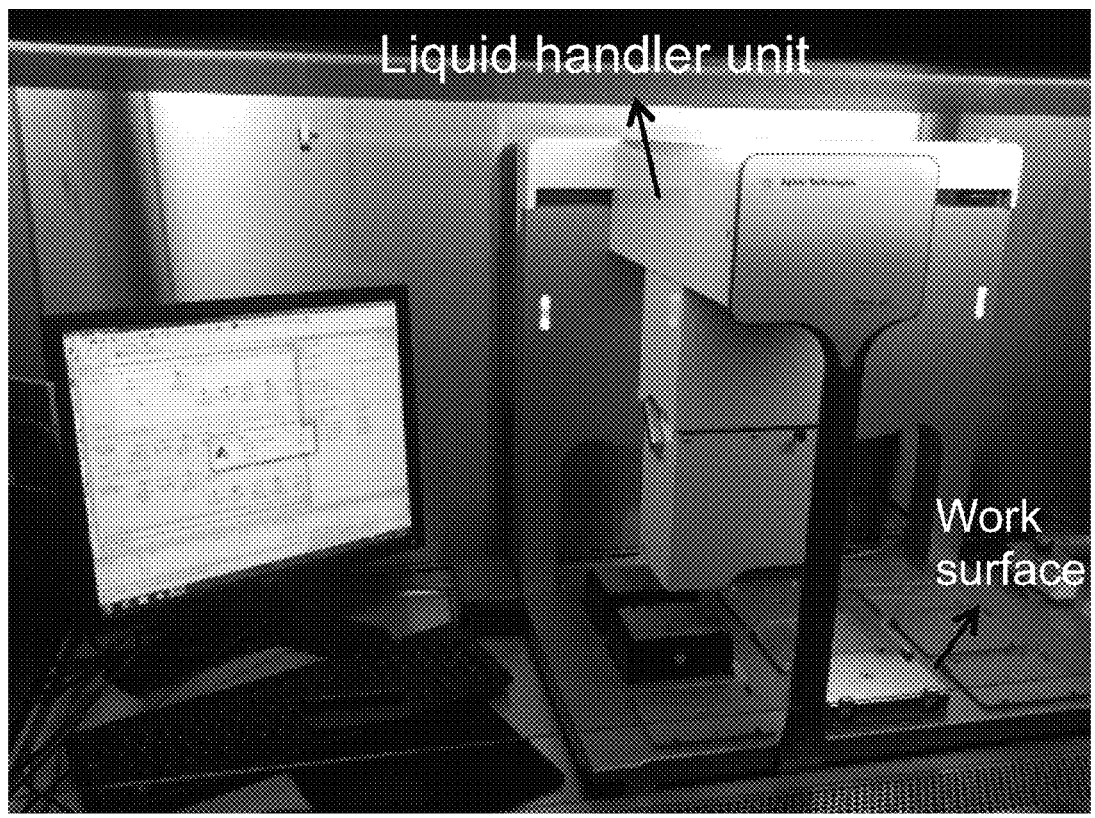
FIG. 2 provides a liquid handler unit with nine work surface stations for holding microwell plates, pipette tip boxes, and a pipette head.
Figure 3:
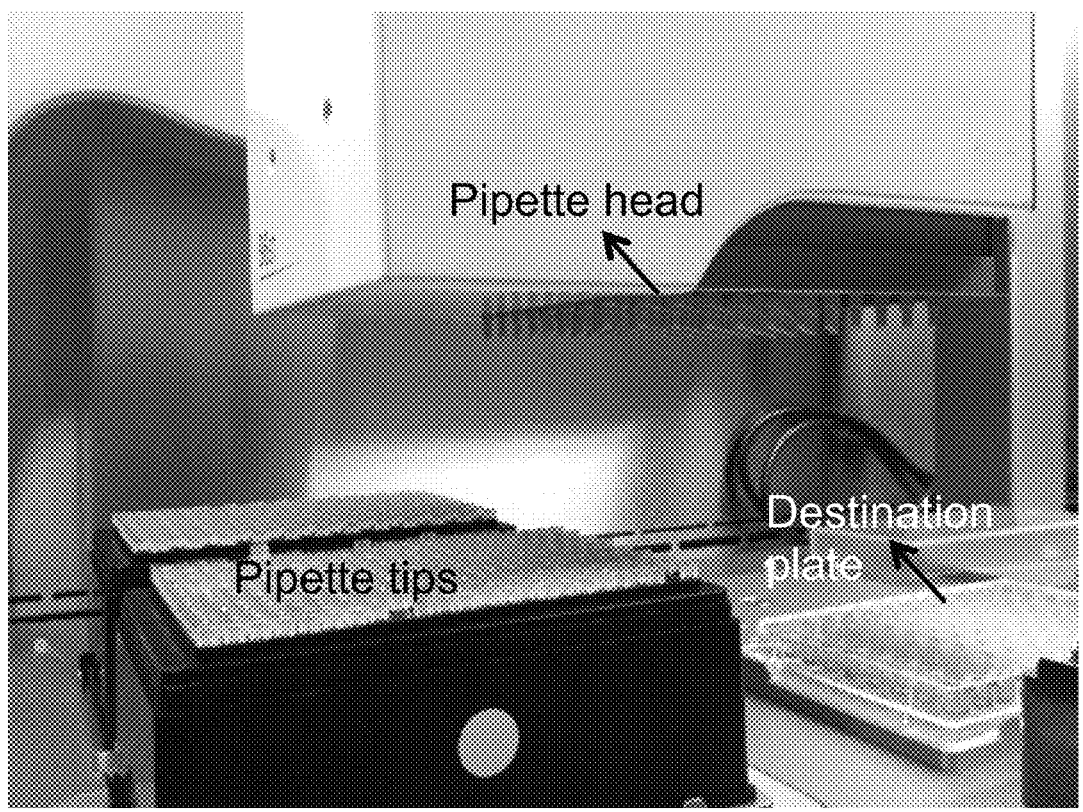
FIG. 3 shows the pipette head of the liquid handler that shows barrels where pipette tips are mounted on. Pipette tips and a destination plate resting on different work surface stations are also shown.

While cellular spheroids may be produced from cells in an aqueous multi-phase system prepared by hand, higher precision may be obtained when a robotic apparatus is employed. In one or more embodiments, at least one step is performed by a robotic apparatus. A robotic apparatus includes the use of a liquid handler unit as seen in FIGS. 2 and 3.

Steps performed by a robotic apparatus may be automated and performed without the assistance of humans. For instance, a liquid handling unit may be programmed to store a plate, retrieve a plate, and refresh the cell culture media at regular intervals such as every three days. Other steps may be included such as a photographing step, where a handling unit may also be programmed to retrieve a plate and photograph the cells in the aqueous multi-phase at regular intervals to chart spheroid progression.

Advantageously, the used of a robotic apparatus allows for cell spheroids to be produced and analyzed in a high-throughput fashion. In these or other embodiments, a plurality of multi-phase systems as described above may be used.

An aqueous multi-phase system may be used in a method to screen potential drugs comprising: providing an aqueous two-phase system for the production of cell spheroids comprising an immersion aqueous polymer phase, and within the immersion aqueous polymer phase, a droplet of a droplet aqueous polymer phase containing a cellular spheroid; administering a potential drug; and monitoring the cellular spheroid.

The term "potential drug" refers to a compound or compounds to be to be analyzed for activity on a cell or cellular spheroid. A potential drug may be administered to the cellular spheroid by introducing the potential drug with the cell media during the creation of the multi-phase polymer system or during a cell media refresh. The potential drug may be administered to the cellular spheroid without cell media in a neat fashion or diluted in a solution.

The cells may be monitored by periodic viewing, and photographing. In one or more embodiment, a stain may be applied to the cells of the cellular spheroid. The stain may be used to assist the visual determination of cell life. A stain useful for determining if the cells are still alive is calcein AM. Other stains may be used to determine if cells are no longer alive, such as ethidium homodimer-1. Assays may also be performed to monitor the effects of potential drugs on the cellular spheroids. Potential assays include, but are not limited to, Alamar blue, Presto blue, and MTT ((3-(4 5-dimethylthiazol-2-yl)-2 5-diphenyltetrazolium bromide).

In one or more embodiments, where a plurality of multiphase systems are used to screen potential drugs, a potential drug may be administered in different concentration. In one or more embodiments, where a plurality of multiphase systems are used to screen potential drugs, a different potential drug may be administered to each multiphase system or groups of multiphase systems within a plurality of multiphase systems. In other embodiments, the same drug my be administered to a plurality of multiphase systems or a plurality of groups of multiphase systems each with a different type of cell.

In order to demonstrate the practice of the present invention, the following examples have been prepared and tested. The examples should not, however, be viewed as limiting the scope of the invention. The claims will serve to define the invention.

EXAMPLES

Figures 4A, 4B:
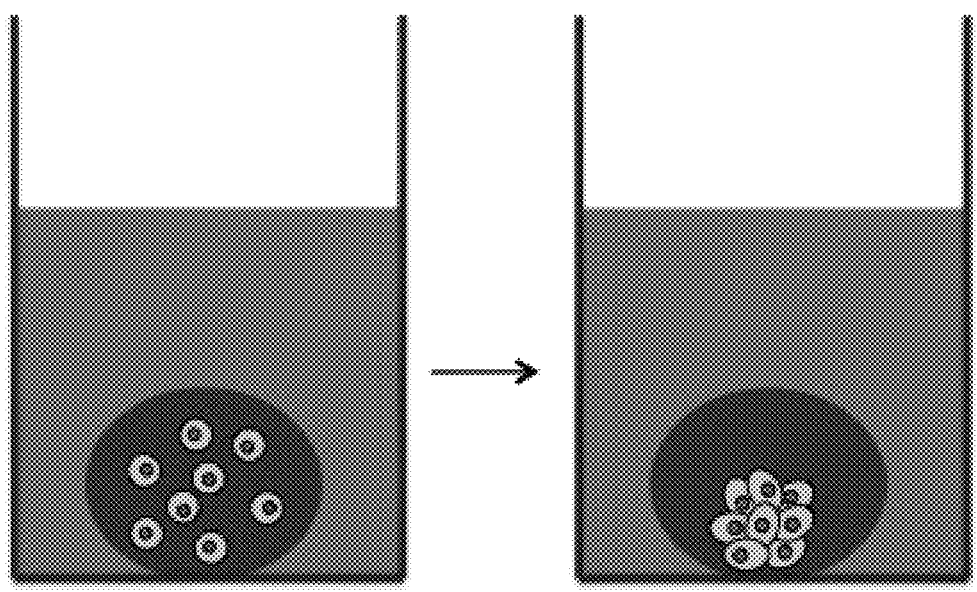
FIG. 4A provides a schematic of a dextran phase drop containing cells immersed in the immersion polyethylene glycol phase.
FIG. 4B provides a schematic of cells within the dextran drop aggregate and form a spheroid.
Figure 5:
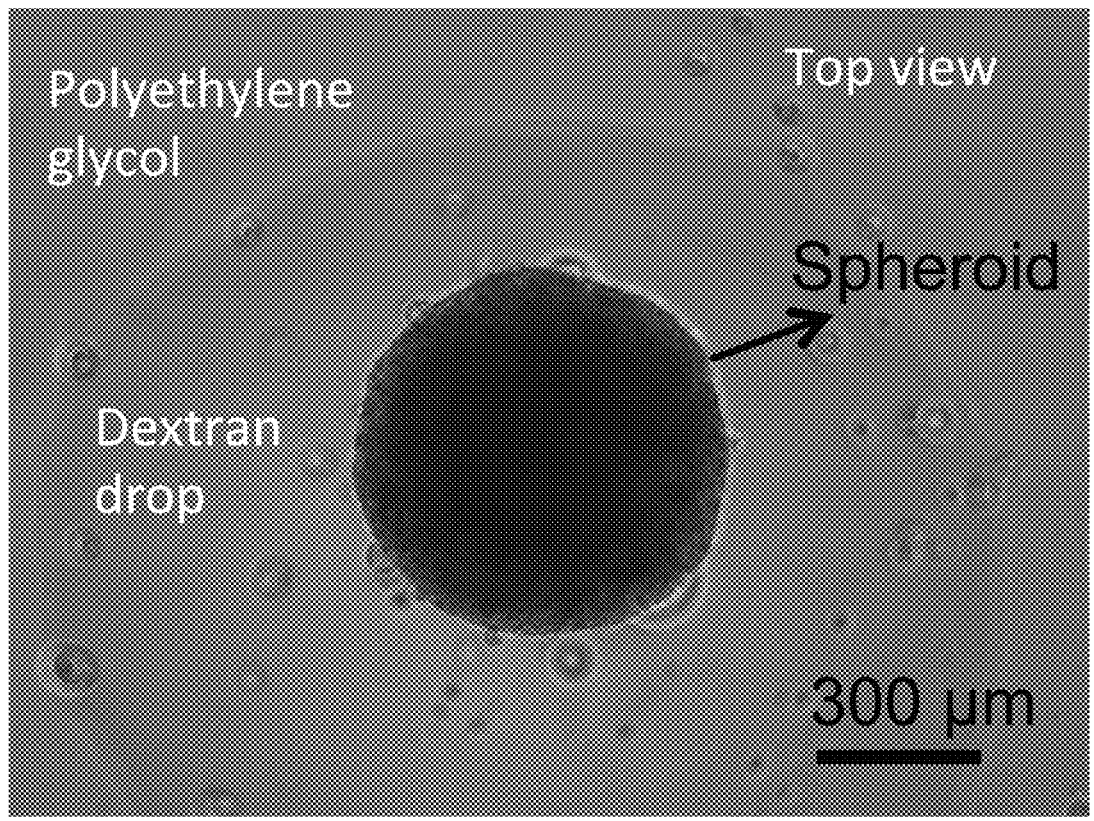
FIG. 5 provides a spheroid of A431.H9 skin cancer cells formed inside the dextran drop immersed in the polyethylene glycol phase. The periphery of the dextran drop is visible.

The Example 1 was prepared using a two-component cell culture media. Component 1 contains 5% (w/w) polyethylene glycol (PEG, Mw: 35,000) and component 2 contains 12.8% (w/w) Dextran (DEX, Mw: 500,000). When mixed, these two components segregate and form two immiscible phases that can be separated (FIG. 1). First, the PEG phase is loaded into wells of a well plate (destination plate) and this plate is placed on the work surface of a robotic liquid handler (FIG. 2). Then cells are harvested from a culture dish, mixed with the DEX phase at a 1:1 volumetric ratio to reduce DEX concentration to 6.4% (w/w), and loaded into a second plate (source plate). This plate is also placed on the work surface of the liquid handler. Pipette tips are mounted onto the dispense head of the liquid handler (FIG. 3) and are immersed into the source plate to load a defined volume (~0.3 microliters) of the cell suspension in DEX phase. After retraction from the source plate, pipette tips are lowered into the destination plate and dispense their content. Dispensed solution forms a single droplet containing cells in each well and the droplet remains immiscible from its surrounding PEG phase (FIG. 4a). Cells aggregate and form an individual spheroid in each well (FIG. 4b and FIG. 5).

TABLE 1

Aqueous Two-Phase Systems that Produced Spheroids

| Example | Top Phase | Bottom Phase |
|---|---|---|
| 2 | 5% PEG 35K | 5% DEX 500K |
| 3 | 5% PEG 35K | 10% DEX 500K |
| 4 | 15% PEG 35K | 10% PAM 10K, 50 wt. % in $H_2O$ |
| 5 | 10% PEG 8K | 10% DEX 500K |
| 6 | 10% PEG 8K | 5% DEX 500K |
| 7 | 20% PEG 8K | 5% DEX 500K |

Table 1 provides a list of other aqueous two-phase systems that produced spheroids. In table 1, the PAM denotes polyacrylamide.

Figure 6:
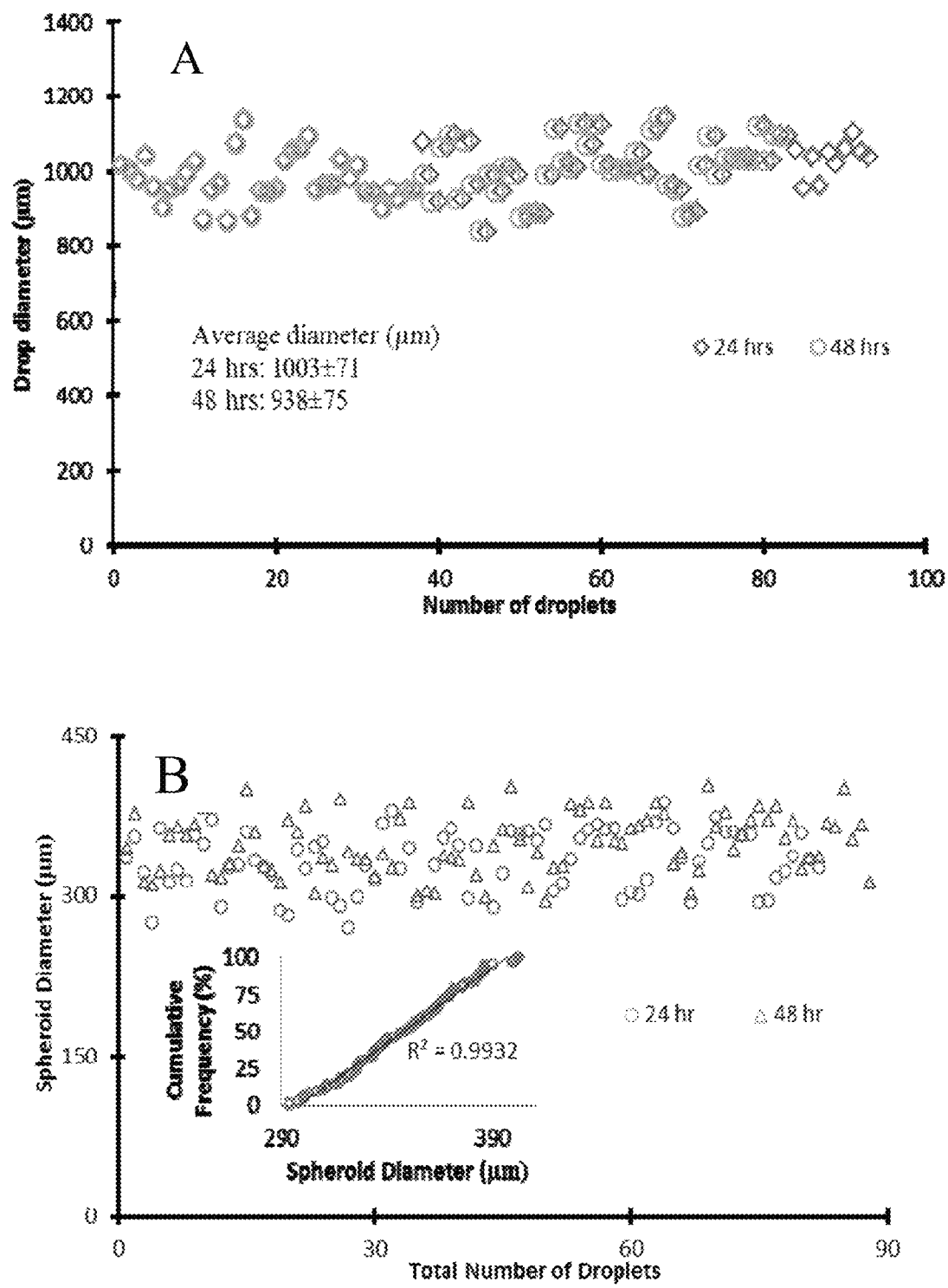
FIG. 6A shows a distribution of diameter of 0.3 microliters DEX drops containing cells after 24 hrs and 48 hrs of incubation.
FIG. 6B shows spheroid diameter distribution after 24 hrs and 48 hrs with average values of 333±28 µm and 349±28 µm, respectively, for DEX drops of 0.3 microliters containing 10,000 skin cancer A431.H9 cells.

The consistency of spheroid size is critical for drug testing and depends on the ability to dispense a well-defined volume of a cell-containing DEX drop in each well. To ensure consistency of DEX-drops, 80 drops of 0.3 microliters containing 10,000 skin cancer cells (A431.H9) are dispensed into PEG solution in individual wells of a 96-well plate and imaged after 24 hrs and 48 hrs. Captured images are analyzed by image processing program, available as ImageJ from the National Institute of Health, for drop and spheroid diameters. FIG. 6A, shows the distribution of drop diameter and gives the average and standard deviations. After 24 and 48 hrs of incubation, the standard deviation of the drop diameter is less than 8%, demonstrating the consistency of our protocol. FIG. 6B, presents the diameter of spheroids that distributes with averages of 333 µm and 349 µm after 24 and 48 hrs, respectively. A standard deviation of smaller than 8.4% in addition to, a linear cumulative curve (inset of FIG. 6B) confirms the normal distribution of spheroids diameter and the consistency of our spheroid formation technique.

Figure 7:
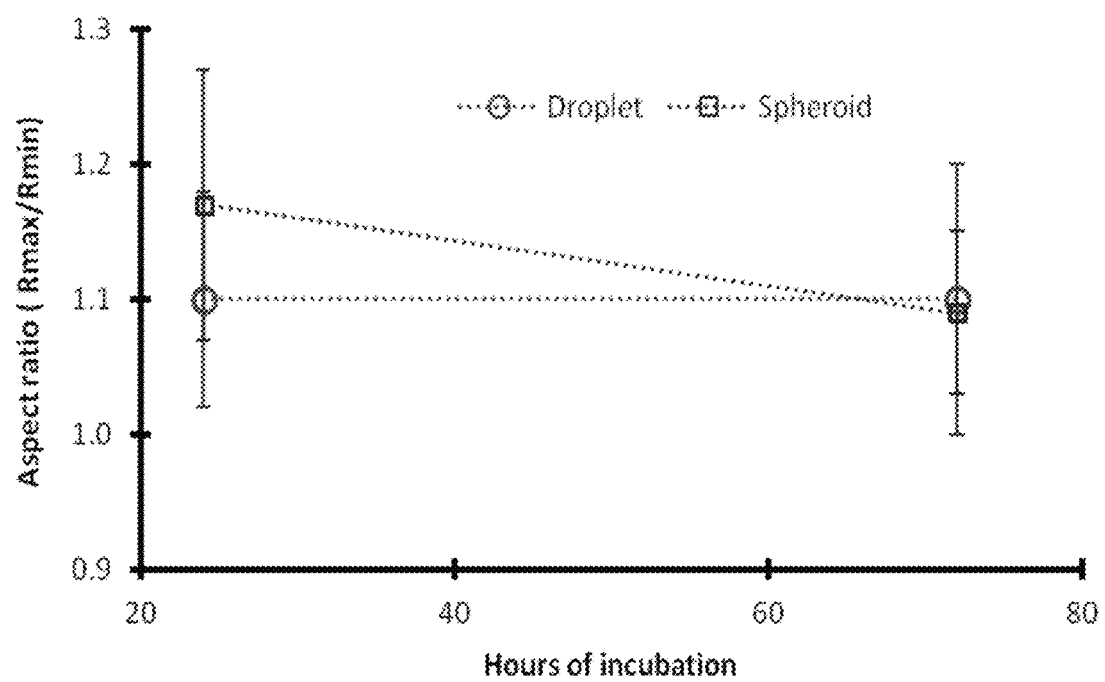
FIG. 7 shows circularity of spheroids and circularity of DEX drops of 0.3 microliters volume after 24 hrs and 72 hrs of incubation. A cell density of 10,000 was used.

To measure the circularity of forming spheroids, the aspect ratio defined as largest versus smallest diameter of a spheroid is compared versus that of DEX drops after 24 hrs and 72 hrs (FIG. 7). Moreover, to ensure viability of spheroids, generated spheroids are stained with cell viability indicating fluorescent dyes. Live cells are stained green with a cell-permeable green fluorescent dye, calcein AM and dead cells are stained with a red fluorescent dye, ethidium homodimer-1. The cell staining showed that cells are mainly stained green indicating the viability of cells. Less green color in the core of the spheroid represents reproducing a physiologic aspect of tumor spheroids that is limitation of diffusion of chemicals including drug compounds to the core of spheroids.

Figure 8:
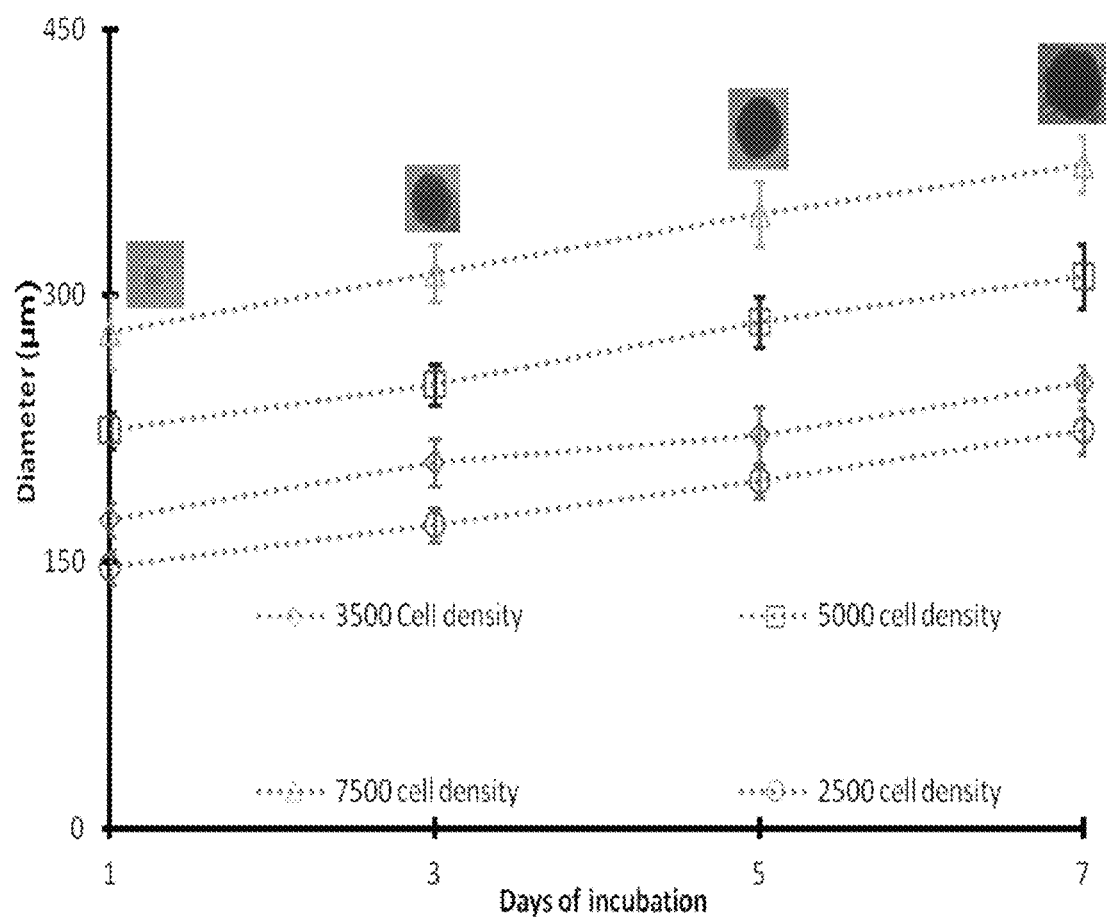
FIG. 8 shows spheroids growth curves for four cell densities over 7 days of incubation.

Another important indication of viability of spheroids generated using ATPS microtechnology is the growth of spheroids during incubation. Over time spheroids grow in size, resembling growth of tumors in cancer patients (FIG. 8). To evaluate the growth patterns of spheroids formed using the ATPS technology, four different cell densities of 2,500, 3,500, 5,000 and 7,500 are studied. Spheroids are produced using 0.2 microliters drops of 6.4% DEX residing within a 5% PEG solution as described above. Spheroids are imaged every other day and 40 µl of fresh media is robotically added to each well after imaging. FIG. 8 shows the growth curves of spheroids for all four cell densities. The diameter of spheroids increases consistently for all densities demonstrating the viability of cells. In addition, spheroids diameter increases with an approximate linear trend for all densities. The percentile growth declines slightly for higher cell densities. For example, the 7,500 cell density spheroids show 35% change in diameter from the 1st to the 7th day whereas the 2,500 density spheroids show 52% change during the same time period. However, spheroids with higher cell densities show more significant growth ratio (slope of growth curve) during the entire experiment. It can be seen that the slope of growth line for the 2,500 cell density spheroids is 12 µm/day whereas for spheroids with 2,500 cell density, the slope is 17 µm/day. This is more prominent after the 3rd day of incubation.

In addition, we show the versatility of this technology for generating spheroids of different cancer cells by studying a metastatic breast cancer cell MDA-MB-157. FIG. 9A-C shows spheroid formation by these cells at different cell densities. Finally, we demonstrate the potential of this tumor spheroid technology for drug screening by treating both A431.H9 and MDA-MB-157 cells with different concentrations of a standard anti-cancer drug, cisplatin up to 333.3 µM for A431.H9 cells and up to 200 µM for MDA-MB-157 cells (Table 2). After incubation for four days, a viability reagent is added to each well and the viability of spheroids is determined through an enzymatic assay available as PRESTO BLUE from Life Technologies Co.

TABLE 2

Percent viabilities and standard errors for
MDA-MB 157 spheroids treated with cisplatin

| Cisplatin Concentration | Percent Viability | Standard Error |
|---|---|---|
| 25 µM | 54.86% | 12.81% |
| 50 µM | 34.31% | 12.21% |
| 100 µM | 30.30% | 9.26% |
| 150 µM | 24.60% | 4.73% |
| 200 µM | 18.81% | 4.42% |

Table 2 represents the viability of treated versus non-treated (control) spheroids against drug concentration produced. The drug, diluted with culture media, was renewed once by the addition of 50 µL after two days of incubation. As displayed in the Table 1, the percent viability results follow a gradual decrease as the cisplatin concentration increases. These results indicate the reliability of this assay technology for high throughput drug testing against cancer cell spheroids.

Various modifications and alterations that do not depart from the scope and spirit of this invention will become apparent to those skilled in the art. This invention is not to be duly limited to the illustrative embodiments set forth herein.

What is claimed is:

1. A method of producing a cellular spheroid comprising:
   providing a well containing an immersion aqueous polymer phase;
   inserting a droplet aqueous polymer phase to form a substantially spherical droplet, where the droplet aqueous polymer phase is immiscible with the immersion aqueous polymer phase;
   inserting cells selected from cancer and stem cells into the droplet aqueous polymer phase; and
   allowing the cells to self assemble into a spheroid.

2. The method of claim 1, where the droplet phase and cells are premixed prior to being inserted into the immersion aqueous polymer phase.

3. The method of claim 1, where at least one step is performed by robotic means.

4. The method of claim 1, where the cells are cancer cells selected from breast cancer, prostate cancer, liver cancer, lung cancer, ovarian cancer, and sarcomas cancer cells.

5. The method of claim 1, where the well is one of a plurality of wells on a well plate.

6. The method of claim 1, where the cellular spheroid is a multicellular spheroid containing at least two different types of cells.

7. The method of claim 1, where the droplet aqueous polymer phase is denser than the immersion aqueous polymer phase.

8. The method of claim 1, where the cellular spheroids are produced in a well with a surface and the substantially spherical droplet has minimal contacts with the surface.

9. The method of claim 1, where the cellular spheroids are produced in a well a well with a surface that is non-adherent to cells.

10. The method of claim 1, where the droplet aqueous polymer phase has a volume percentage of the total aqueous multi-phase system less than 0.02%.

11. The method of claim 1, where the droplet aqueous polymer phase has a volume percentage of the total aqueous multi-phase system of about 0.0001% to about 0.02% the total aqueous multi-phase system.

12. A method of producing a cellular spheroid comprising:
   providing a well containing an immersion aqueous polymer phase;
   inserting a droplet aqueous polymer phase to form a droplet with a high contact angle, where the droplet aqueous polymer phase is immiscible with the immersion aqueous polymer phase;
   inserting cells selected from cancer and stem cells into the droplet aqueous polymer phase; and
   allowing the cells to self assemble into a spheroid.

* * * * *